US00PP35676P2

(12) United States Plant Patent
Bennett

(10) Patent No.: US PP35,676 P2
(45) Date of Patent: Mar. 12, 2024

(54) ***ROSA HYBRIDA* SHRUB NAMED 'AUSPERIDOT'**

(50) Latin Name: *Rosa hybrida*
Varietal Denomination: AUSperidot

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 18/445,061

(22) Filed: Mar. 24, 2023

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 5/02
See application file for complete search history.

*Primary Examiner* — Keith O. Robinson

(57) ABSTRACT

A variety of rose plant of the shrub class, named 'AUSperidot'. The 'AUSperidot' is a variety of a cut rose bearing large blooms with a white blend color and a light fragrance with a long vase life.

1 Drawing Sheet

Classification: The present invention relates to a new *Rosa hybrida* shrub of the market class 'English Rose'.

Variety denomination: The new plant has the varietal denomination 'AUSperidot'.

ORIGIN OF INVENTION

This invention relates to a new and distinct variety of shrub rose plant named 'AUSperidot', which was originated from the cross-pollination of the two 'unnamed' and unpatented seedlings of *Rosa hybrida.*

BACKGROUND OF THE INVENTION

The primary objective of this breeding was to produce a cut rose variety bearing large blooms with a white blend color and a light fragrance with a long vase life.

SUMMARY OF THE INVENTION

Among the features which distinguish the new variety from others presently available and commercial rose cultivars known to the inventor is the following combination of characteristics: very pale, almost white colored roses with many petalled, very large double blooms, strong stems, a light fragrance and growth habit suitable for cut rose production.

Asexual reproduction of the new variety by stem cutting as performed in Albrighton, United Kingdom shows that the foregoing and other distinguishing characteristics come true to form and are established and transmitted through succeeding asexual propagations. 'AUSperidot' may be asexually propagated by stem cutting.

COMPARISON WITH PARENTS

The maternal and paternal parents of 'AUSperidot' are two unnamed seedlings. The new rose may be distinguished from its seed parent, by the following combination of characteristics: the seed parent has a flower which is yellow blend in color, with smaller leaves, whereas 'AUSperidot' is a very pale, almost white color with larger leaves. The new rose may be distinguished from its pollen parent, by the following combination of characteristics: the pollen parent is yellow in color with a more informal shapeless bloom and a much higher quantity of prickles, whereas 'AUSperidot' is almost white in color with a more rounded bloom shape and fewer prickles.

COMPARISON WITH THE CLOSEST COMMERCIALLY AVAILABLE CULTIVAR

The most similar rose variety is 'AUSwagsy' (U.S. Plant Pat. No. 32,531). 'AUSwagsy' typically has more petals (approx. 105) than 'AUSperidot' (approx. 86). 'AUSwagsy' also exhibits a glossier upper side of the leaf when compared to 'AUSperidot', which is more matt/dull. 'AUSwagsy' exhibits pink stigma (RHS N66C), whereas 'AUSperidot' has yellow stigma (RHS 3B). Finally, 'AUSwagsy' has a medium/moderate fragrance of citrus, whereas for 'AUSperidot' the fragrance is weak/slight and more of tea.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of cut 'AUSperidot' specimens were made at a garden in Albrighton, Wolverhampton, United Kingdom. The following description is of 4-year-old rose plants of the new variety grown in a greenhouse environment in Albrighton, United Kingdom in the month of April. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 4 cm long and 2 to 2.5 cm in diameter when the petals start to unfurl.

*Form*.—The bud form is long pointed ovoid, with a lower portion that is flattened convex.

*Color*.—When sepals first divide, the bud color is RHS 10A (yellow group). When half blown, the upper sides of the petals are RHS 11B (yellow group), and the lower sides of the petals are between RHS 5D (yellow group) and RHS 155A (white group).

*Calyx*.—Shape: opens as a star shape and folds back against the stem. Length: 7 cm. Diameter: 7 cm.

*Sepals*.—Arrangement: Regular. Color: Upper Surface: RHS 138B (green group). Lower Surface: RHS 143A (green group). Length: 3 cm. Width: 1 cm. Shape: Lanceolate. Apex: Lanceolate. Margin: Smooth. Surface texture: Upper Surface: Glandular. Lower Surface: Hairy. Number: There are 3 lightly appendaged sepals, and 2 unappendaged sepals with hairy edges.

*Receptacles*.—Color: RHS 144A (yellow-green group). Shape: Pitcher. Size: Medium, about 1.2 cm long×0.8 cm wide. Surface: Smooth.

*Peduncle*.—Length: Long, averaging about 6.5 cm. Surface: Glandular. Color: RHS 144B (green-yellow group). Strength: Normal.

Blooms:

*Size*.—Large, average open diameter is about 10 cm and average depth is about 3.2 cm.

*Borne*.—Singly with the other blooms being nipped out for single bloom cut rose production.

*Form*.—When first open, bloom is cupped. Permanence of bloom flattens: outer petals curl slightly.

Petalage: Number of petals under normal conditions: approx. 86.

*Color*.—The upper sides of the petals are RHS N155D (white group). The reverse sides of the petals are RHS N155D (white group). The base of the petals has a very small to small basal spot that is RHS 2A (yellow group) in color.

*Variegations*.—None.

*Discoloration*.—The general tonality at the end of the first day is RHS 11B (yellow group), and at the end of the third day is RHS N155D (white group).

*Fragrance*.—Slight. Character of fragrance: Tea.

Petals:

*Texture*.—Smooth, satiny on both sides.

*Size*.—Width: 3.7 cm. Length: 4.7 cm.

*Surface*.—Smooth.

*Shape*.—Round (outer petals); Obovate (inner petals).

*Margin*.—Entire.

*Apex shape*.—Rounded.

*Base shape*.—Acute.

*Form*.—Outer petals flat, inner petals slightly recurved.

*Arrangement*.—Informal.

*Petaloids*.—Number: Few — typically 10-12. Color: RHS 4D (yellow group). Length: 1.8 cm. Width: 1 cm. Shape: Obovate. Margin: Irregular.

*Persistence*.—Petals drop off cleanly before drying.

*Lastingness*.—On the plant: not tested. As a cut flower: long about 9 days.

Reproductive parts:

*Stamens*.—Number: approximately 70-75. Length: approximately 0.8 cm.

*Anthers*.—Length: approximately 0.6 cm. Color: RHS 16B (yellow-orange group). Arrangement: Regular around styles.

*Filaments*.—Color: RHS 13A (yellow group). Length: 0.2 cm.

*Pollen*.—Color: RHS 16B (yellow-orange group). Amount: Scarce.

*Pistils*.—Number: approximately 75. Length: approximately 0.6 cm.

*Styles*.—Color: RHS 2C (yellow group). Length: 0.5 cm.

*Stigmas*.—Color: RHS 3B (yellow group). Length: approximately 0.1 cm.

*Hips*.—NONE Observed.

PLANT CHARACTERISTICS

Plant form: Shrub.

Plant growth: Vigorous and upright.

Age to maturity: 2 years.

Mature plant: Height: 140 cm. Width: 60 cm.

Rootstock: Own root (production from cuttings) for the roses observed in the United Kingdom.

Foliage:

*Number*.—Leaflets on normal mid-stem leaves is: 5 with instances of 7 (including terminal leaflet).

*Size*.—Very large to large, about 19.5 cm long×12.6 cm wide.

*Quantity*.—Normal. Number of leaves per flowering stem is: approximately 7-8.

*Color*.—New foliage: Upper side: RHS N186C (greyed purple group) with RHS 144A (yellow-green group). Lower side: RHS 187C (greyed-purple group). Old foliage: Upper side: RHS 147A (yellow-green group). Lower side: RHS 191A (greyed-green group).

Leaflets:

*Size*.—About 6.6 cm long×4.5 cm wide.

*Shape*.—Pointed oval.

*Base shape*.—Usually rounded, occasionally cordate.

*Apex shape*.—Acuminate.

*Texture*.—Upper side: Leathery. Lower side: Leathery.

*Glossiness*.—Weak/Matte.

*Edge*.—Serrated.

*Serrations*.—Single.

*Petiole*.—Color: Perimeter is RHS 146B (yellow-green group), and central is RHS 145B (yellow-green group). Length: 5.7 cm. Width: 0.15 cm. Upper Surface Texture: Smooth. Lower Surface Texture: Smooth with a few prickles.

*Petiole rachis*.—Color: perimeter is RHS 146B (yellow-green group), and center is RHS 145B (yellow-green group). Underside: rough with prickles. Upperside: smooth.

*Stipules*.—Length: 2 cm. Shape: Lateral. Descriptor: Glandular. Apex: Acute. Color: RHS 137B (green group).

*Auricle*.—Shape: Lanceolate. Length: 0.3 cm Width: 0.1 cm. Color: RHS N138A (green group).

*Vein color*.—Same as leaf color.

*Venation pattern*.—Reticulate.

Wood:

*New wood*.—Color: RHS 148A (yellow-green group) with RHS 183A (greyed-purple group) at the tip of new growth. Bark: Smooth.

*Old wood*.—Color: RHS 146A (yellow-green group). Bark: Smooth.

Branching habit:

*Number*.—Not applicable.

*Dimensions*.—Not applicable.

Stems:

*Mature stem*.—Length: 130 cm. Diameter: 0.8 cm.

*Internode distance*.—7.5 cm. The above measurements are all variable, depending on growing conditions in a season.

*Stem pubescence present*.—No.

Prickles:

*Quantity*.—On main canes from base: few. Number per stem length: 5-10 per 20 cm.

*Form*.—Hooked downward/deep concave.

*Length*.—0.5 cm.

*Color when young*.—RHS N182A (greyed-red group) at base and middle, RHS 160A (greyed-yellow group) at tip.

*Color when mature*.—RHS N162A (greyed-yellow group) with a tinge of RHS 70C (red-purple group).

Small prickles:

*Quantity*.—Main stalk: Few. Number per stem length: 1-2 per 20 cm. Laterals: not applicable.

*Color*.—When young: RHS N182A (greyed-red group) at base and middle, RHS 160A (greyed-yellow group) at tip. When mature: RHS N162A (greyed-yellow group) with a tinge of RHS 70C (red-purple group).

Disease Resistance:

*Powdery mildew* (*podosphaera pannosa*).—Resistant.

*Downy mildew* (*peronospora species*).—Resistant.

*Blackspot* (*diplocarpon rosae*).—Resistant.

*Rust* (*phragmidium tuberculatum*).—Resistant.

Pest resistance: Not tested.

Winter hardiness: Not tested.

Growing conditions: Normal greenhouse conditions for cut rose production.

What is claimed is:

1. A new and distinct variety of rose plant of the shrub class, named 'AUSPERIDOT', substantially as herein shown and described.

* * * * *

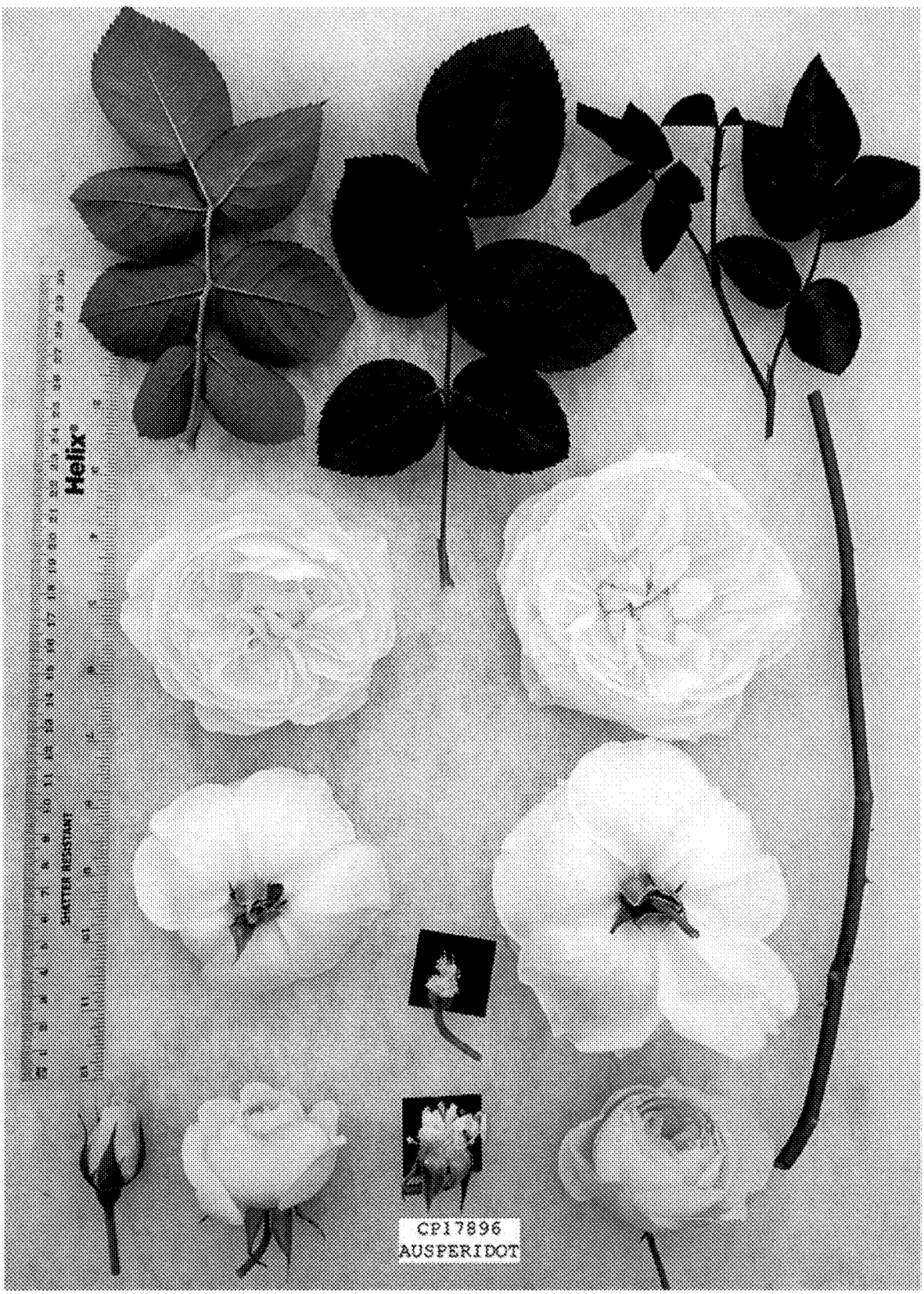
Helix
SHUTTER RESTRAINT
CP17896
AUSPERIDOT